(12) United States Patent
Shibata

(10) Patent No.: US 6,827,724 B2
(45) Date of Patent: Dec. 7, 2004

(54) ULTRASONIC VIBRATOR CAPABLE OF INFALLIBLY PREVENTING DROPS OF WATER FROM ENTERING THE INSIDE OF A CASING OF THE VIBRATOR EVEN IF AUTOCLAVE STERILIZATION WITHOUT A DRYING PROCESS IS PERFORMED

(75) Inventor: Norikiyo Shibata, Yamato (JP)

(73) Assignee: Olympus Corporation (JP)

( * ) Notice: Subject to any disclaimer, the term of this patent is extended or adjusted under 35 U.S.C. 154(b) by 373 days.

(21) Appl. No.: 10/152,362

(22) Filed: May 20, 2002

(65) Prior Publication Data

US 2002/0143321 A1 Oct. 3, 2002

Related U.S. Application Data

(62) Division of application No. 09/587,847, filed on Jun. 6, 2000, now Pat. No. 6,416,525.

(30) Foreign Application Priority Data

Jun. 8, 1999 (JP) .......................................... 11-161393
Jul. 9, 1999 (JP) .......................................... 11-196511

(51) Int. Cl.$^7$ .............................................. A61B 17/00
(52) U.S. Cl. ......................................... 606/169; 604/22
(58) Field of Search ................................. 606/169, 170, 606/171, 174, 180; 604/22, 48

(56) References Cited

U.S. PATENT DOCUMENTS 5,935,143 A * 8/1999 Hood ......................... 606/169
5,989,275 A * 11/1999 Estabrook et al. .......... 606/169

* cited by examiner

Primary Examiner—Kevin T. Truong
(74) Attorney, Agent, or Firm—Ostrolenk, Faber, Gerb & Soffen, LLP

(57) ABSTRACT

An ultrasonic vibrator has a very versatile, simple structure without a rotational structure. In order to infallibly prevent drops of water from entering the inside of the casing of the vibrator even if autoclave sterilization is performed without a drying process, the ultrasonic vibrator has a connecting member and a partition member, each used as a barrier plate member making up the inside of the vibrator body. The ultrasonic vibrator additionally has O-rings disposed in a packing, an electrode, and an airtight cap. By the O-rings, water is prevented from entering a lumen of a transducer. The electrode is insulated by a sealing agent, and a short circuit is presented.

4 Claims, 18 Drawing Sheets

ULTRASONIC VIBRATOR CAPABLE OF INFALLIBLY PREVENTING DROPS OF WATER FROM ENTERING THE INSIDE OF A CASING OF THE VIBRATOR EVEN IF AUTOCLAVE STERILIZATION WITHOUT A DRYING PROCESS IS PERFORMED

RELATED APPLICATIONS

This is a division of U.S. patent application Ser. No. 09/587,847, filed Jun. 6, 2000, now U.S. Pat. No. 6,416,525, in the name of Norikiyo Shibata and entitled Ultrasonic Vibrator Capable of Infallibly Preventing Drops of Water From Entering the Inside of a Casing of the Vibrator Even if Autoclave Sterilization Without a Drying Process is Performed.

This application claims benefit of Japanese Application No. Hei 11-161393 filed in Japan on Jun. 8, 1999, and Japanese Application No. Hei 11-196511 filed in Japan on Jul. 9, 1999, the contents of which are hereby incorporated by reference.

BACKGROUND OF THE INVENTION

1. Field of the Invention

This invention relates to an ultrasonic vibrator for generating ultrasonic vibrations by supplying a high frequency current to a vibrating element.

2. Description of Related Art

Recently, the use of an ultrasonic surgical apparatus, which comprises an ultrasonic vibrator, by which various surgical operations are performed, such as destruction of a calculus or removal of a tumor, has come into practical use. The ultrasonic surgical apparatus comprises a handpiece in which the ultrasonic vibrator is incorporated, and a driving power supply unit that is connected to the handpiece and supplies a driving current to the ultrasonic vibrator.

The ultrasonic surgical apparatus for surgical operations can be used in an abdominal operation or a laparoscopic operation generally by attaching various probes to a device (i.e., vibrator) that receives a high frequency current from a power-supply unit, and generates ultrasonic vibrations.

This type of surgical apparatus must be sterilized because it is handled by a surgeon directly with his/her hand. The vibrator of the ultrasonic surgical apparatus must also be subjected to autoclave sterilization.

Such a vibrator is disclosed in, for example, U.S. Pat. No. 5,395,240, Japanese Patent Publication No. Hei 7-106206, and Japanese Laid-open Patent Publication No. Hei 10-127655.

There are many kinds of autoclave sterilization methods, each determined by a combination of parameters of time, pressure, temperature, etc., in a vacuum drawing step, a sterilizing step, a drying step, and so on.

The ultrasonic vibrator is not adaptable to all these autoclave sterilization methods. Normally, autoclaving includes the cycle of vacuum drawing, sterilizing, and drying steps. At times the autoclaving is urgently performed when the surgical apparatus is carelessly dropped onto a floor during surgery.

In such event, the vacuum drawing and sterilizing steps is performed and the drying step is omitted to save time. By omitting the drying step often causes steam that has entered the casing is not completely expelled therefrom, and, accordingly, the steam collects in the form of drops of water in the casing, for example, in the casing of a vibrator disclosed in Japanese Patent Publication No. Hei-106206. If ultrasonic vibrations are started under this state, in a bolt-fastened Langevin vibrator (transducer), the drops of water adhere between electrodes between which a PZT (lead zirconate titanate) is disposed, and a short circuit is caused, thus decreasing the conversion efficiency of the ultrasonic wave.

When autoclave sterilization is simply performed in a small medical institution, the autoclave sterilization often does not include the drying step. Also, in this situation, as in the previous situation, drops of water collect in the casing, and, as a result, in a bolt-fastened Langevin vibrator (transducer), the water adheres between electrodes between which a PZT (lead zirconate titanate) is disposed, and a short circuit is caused, thus decreasing the conversion efficiency of the ultrasonic wave.

The invention of U.S. Pat. No. 5,395,241 is a magnetostrictive vibrator (transducer), and therefore no problem occurs even if the inside thereof is intentionally subjected to autoclave sterilization. However, the magnetostrictive vibrator is inferior in washability. From the viewpoint of the reduction in the size of a vibrator, a bolt-fastened Langevin type vibrator (transducer) is greatly superior thereto.

In the invention of Japanese Laid-open Patent Publication No. Hei 10-127655, steam does not enter the inside of a vibrator when autoclave sterilization without a drying step is performed, and therefore the conversion-efficiency of ultrasonic vibrations does not decrease. However, there is a drawback in that smooth rotation cannot be made because an O-ring is used for a rotation slide portion, and there is a concern that electric contact will become unreliable because an electric contact portion is rotating. Additionally, there is a drawback in that the weight of the vibrator increases, and the outer diameter thereof is enlarged because the internal structure of the vibrator becomes complex. From the viewpoint of the versatility of the vibrator, the structure of the vibrator should be simple, of course.

In this type of ultrasonic surgical apparatus, the ultrasonic vibrator is driven at a resonance point in order to efficiently perform the surgery. Specifically, when the ultrasonic vibrator is driven, an oscillation frequency is controlled so that a phase difference between a voltage applied to the ultrasonic vibrator and a flowing current reaches zero by the use of PLL (phase-locked loop), and thereby the resonance point is pursued.

By the way, an equivalent circuit of the ultrasonic vibrator generally has a structure in which a braking condenser (braking capacitive component) is connected in parallel with a series resonance circuit in which a coil L, a condenser C, and a resistor R are connected in series. When a voltage is applied to such an ultrasonic vibrator, a current flows through both the braking condenser and the series resonance circuit. However, only the current flowing through the series resonance circuit of the two is converted into ultrasonic vibrations. Therefore, it is most efficient to drive the vibrator at the resonance point (mechanical resonance point) of the series resonance circuit.

Concerning a technique to drive the series resonance circuit at its resonance point (mechanical resonance point), many proposals have been offered heretofore. For example, in Japanese Patent No. 2,898,010, a composite capacitance value in a handpiece is kept constant, and a capacitive component (condenser) by which the composite capacitance value is equalized with an inductance of an inductive component (inductor) L of a driving power-supply unit, is connected in parallel with a ultrasonic vibrator. In other words, the difference in the size of a capacity susceptance of a braking condenser, which various types of ultrasonic vibrators each possess, is compensated by the capacitive component. According to this structure, the composite capacitance value is kept constant even if the ultrasonic vibrators of the handpieces connected to the driving power-supply unit are of different types. In other words, even if the ultrasonic vibrators that are different from each other in the size of the capacity susceptance of the braking condenser are each connected to one inductor, namely, a common driving power-supply unit, the capacity susceptance of the braking condenser is always offset definitely (hereinafter, designated as "matching"). As a result, a resonance frequency peculiar to the ultrasonic vibrator coincides with a driving frequency of the driving power-supply unit.

However, if the ultrasonic vibrator and the capacitive component (condenser) are combined with each other, as described above, so as to bring about matching with respect to the driving power-supply unit, matching must be renewed by, for example, inspection or measurement when either the ultrasonic vibrator or the capacitive component (condenser) is repaired or replaced. This results in more complicated repairing and replacing operations requiring a great deal of labor.

SUMMARY OF THE INVENTION

It is an object of the present invention to, in a bolt-fastened Langevin type ultrasonic transducer, provide an ultrasonic vibrator that has a very versatile, simple structure which does not include a rotational structure, and is capable of infallibly preventing drops of water from entering the inside of the casing of the vibrator even if autoclave sterilization without a drying process is performed.

It is another object of the present invention to provide an ultrasonic vibrator capable of being easily replaced or repaired without performing an adjustment for offsetting the capacity susceptance of a braking condenser of the ultrasonic vibrator with respect to the inductor of a driving power-supply unit.

An ultrasonic vibrator of the present invention is characterized in that it comprises a transducer constructed by connecting a plurality of vibrating elements for converting a driving current into vibrations; an amplitude increasing portion for increasing an amplitude of a vibration of the transducer, the amplitude increasing portion having a horn at a front side thereof and a flange-shaped fixing portion at a base side thereof, the transducer being connected to the flange shaped fixing portion side; a cover covering the transducer; a supporting/fixing member for supporting and fixing the flange-shaped fixing portion to the cover in an airtight state by interposing a packing between the flange-shaped fixing portion and the cover; a lead wire for supplying the driving current to the plurality of vibrating elements; a partition member, disposed at the base side of the transducer, for defining a first chamber for passing the lead wire in an airtight state and containing the transducer in the cover in an airtight state; a member, fitted to a base side of the cover in an airtight state, for defining a second chamber for passing an electric power supply cord in an airtight state and drawing the electric power supply cord into the cover between the partition member and the member; and a plug for connecting the electric power supply cord to an electric power for generation of the driving current.

Other objects and advantages of the present invention will become sufficiently apparent from the detailed description given below.

BRIEF DESCRIPTION OF THE DRAWINGS

FIG. 1 shows the external appearance of an ultrasonic vibrator; FIG. 2 is an exploded view showing the decomposition/deployment of a vibrator body of FIG. 1; FIG. 3 is a sectional view of section 3—3 of the vibrator body of FIG. 1; FIG. 4 is a view showing the structure of a terminal provided in a transducer of FIG. 2, and FIG. 5 shows the vibration distribution of the ultrasonic vibrator of FIG. 1 and the positional relationship of the inside of the vibrator body.

FIG. 7 is a view showing the external appearance of the tip end of a vibrator body; FIG. 8 is a view showing the external appearance of the base end of the vibrator body of FIG. 7; FIG. 9 is an exploded view showing the decomposition/deployment of the vibrator body of FIG. 7; FIG. 10 is an axially sectional view of the vibrator body of FIG. 7, and FIG. 11 is an axially sectional view of a modification of the vibrator body of FIG. 7.

FIG. 12 is a perspective view of an ultrasonic vibrator unit; FIG. 13 is a side sectional view of a handpiece of the ultrasonic vibrator unit of FIG. 12; FIG. 14 is a cross sectional view along line 14—14 of FIG. 13; FIG. 15 is a cross sectional view along line 15—15 of FIG. 13; FIG. 16 is a cross sectional view along line 16—16 of FIG. 13; FIG. 17 is a schematic electrical circuit diagram of the ultrasonic vibrator unit of FIG. 12; FIG. 18 is an exploded sectional view of the ultrasonic vibrator unit of FIG. 12; FIG. 19 is a side sectional view of a modification of the handpiece of the ultrasonic vibrator unit; FIG. 20 is a side sectional view of a plug extending from the handpiece of FIG. 19; FIG. 21 is a perspective view showing another structure of the ultrasonic vibrator, and FIG. 22 is a perspective view showing the inside of a case provided in a cord of the ultrasonic vibrator of FIG. 21.

DETAILED DESCRIPTION OF THE PREFERRED EMBODIMENTS

Embodiments of the present invention will be described hereinafter with reference to the attached drawings.

Embodiment 1

Structure

Figure 1:
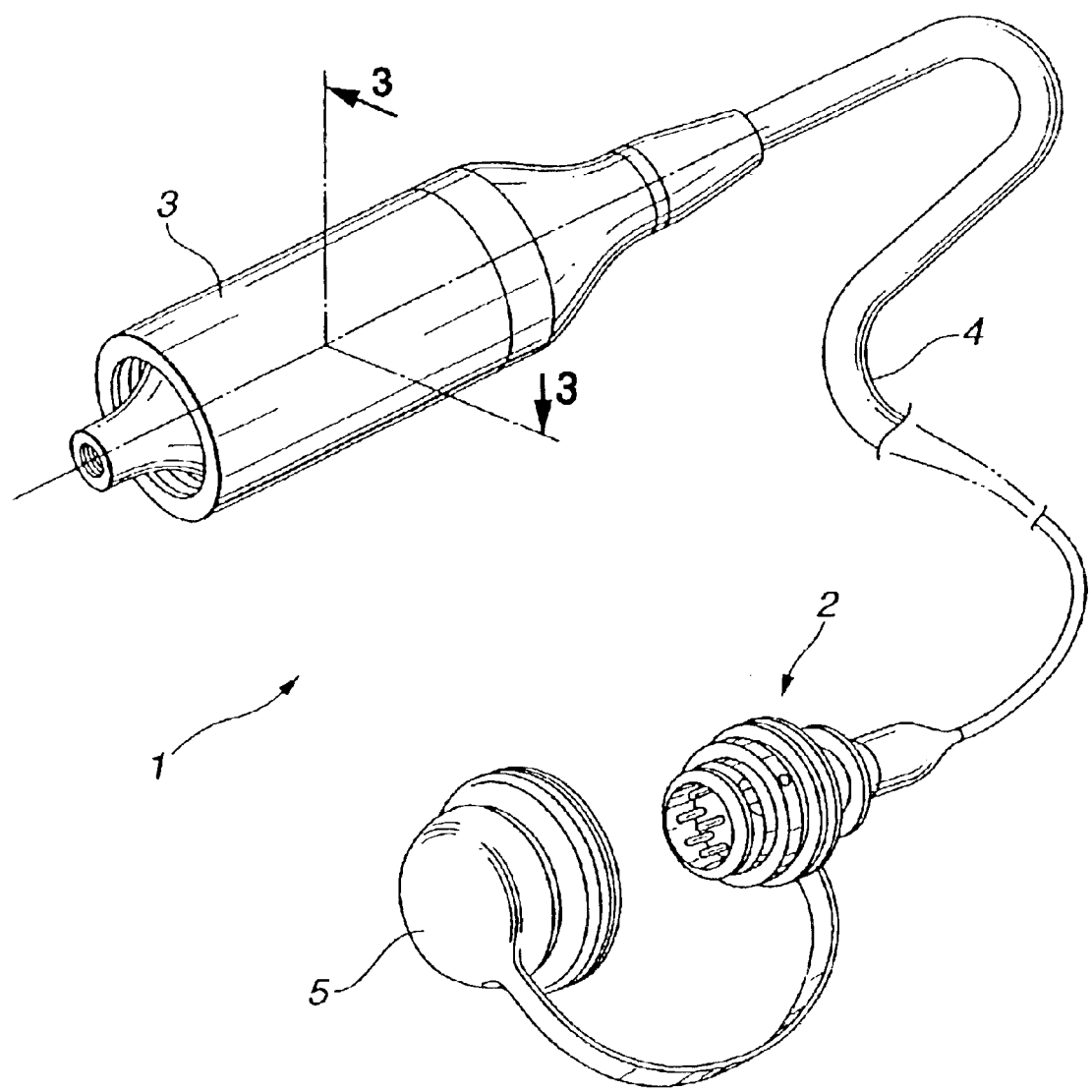
FIGS. 1 to 5 show a first embodiment of the present invention.

As shown in FIG. 1, an ultrasonic vibrator 1 according to this embodiment includes: a plug 2 to be connected to a generator (not shown) that generates a driving current for allowing the ultrasonic vibrator 1 to start ultrasonic vibrations; a cord 4 for sending the driving current from the plug 2 to a vibrator body 3, and a waterproof cap 5 for preventing water from entering the inside of the plug 2 when the ultrasonic vibrator 1 is washed.

Figure 2:
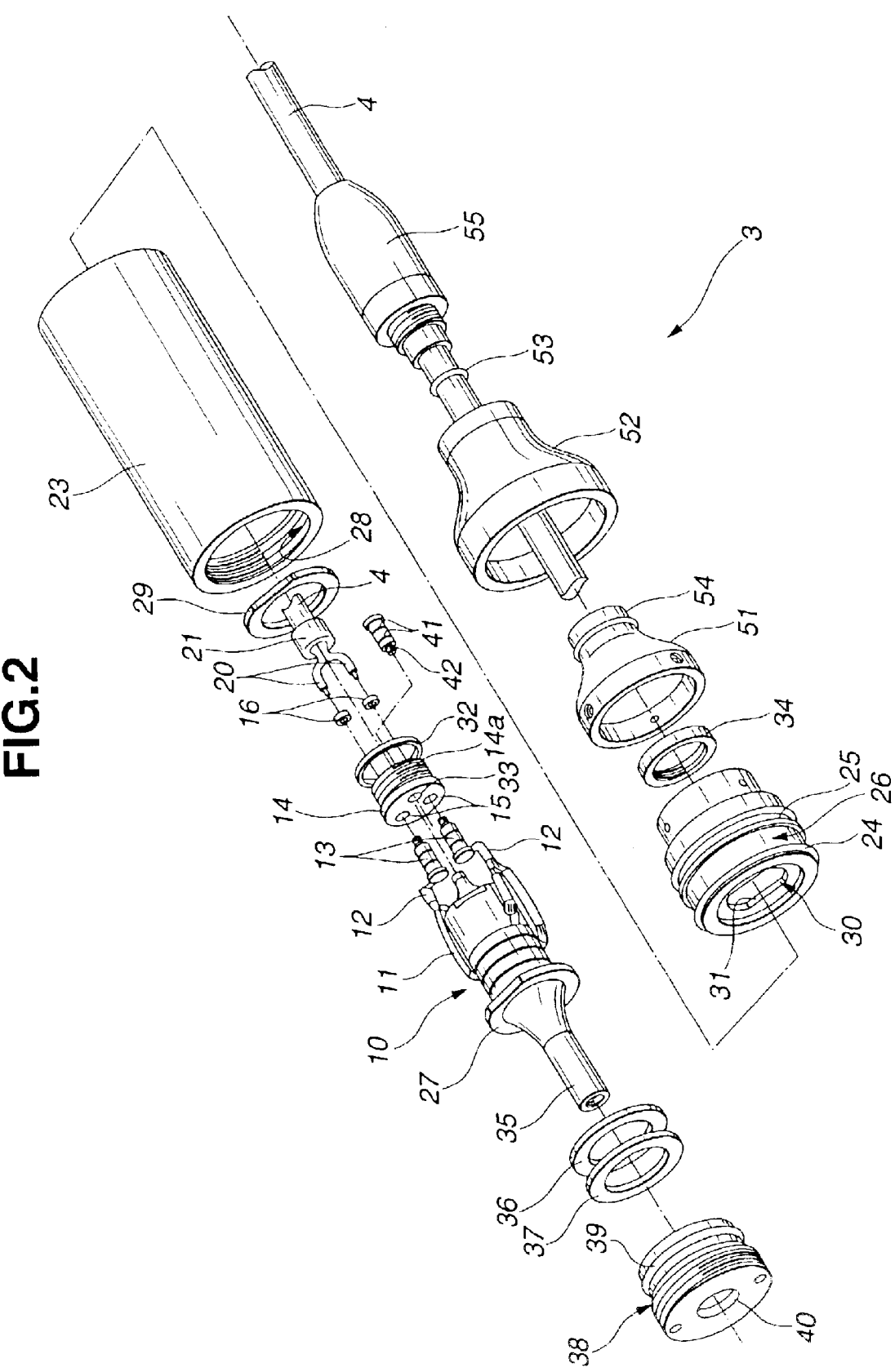
Figure 3:
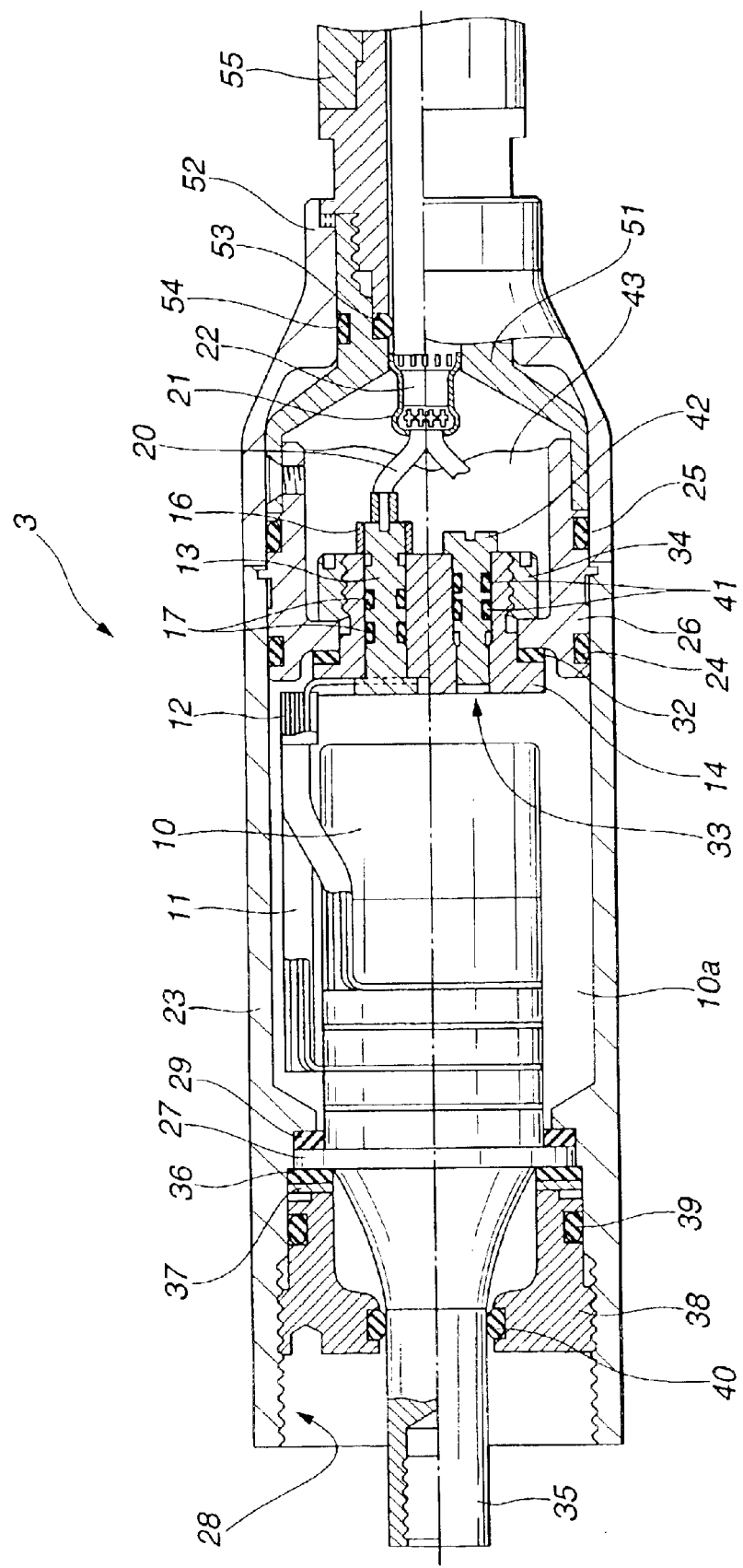

FIG. 2 is an exploded view of the vibrator body 3 of FIG. 1, and FIG. 3 shows section ABC of the vibrator body 3 of FIG. 1.

As shown in FIGS. 2 and 3, a transducer 10 that converts the driving current sent from the generator (not shown) into ultrasonic vibrations is mounted in the vibrator body 3. An end of an electric wire 11 whose coating is peeled off is fixed to the transducer 10 with solder. The other end of wire 11 whose coating is also peeled off is fixed to a terminal 12 with solder.

Figure 4:
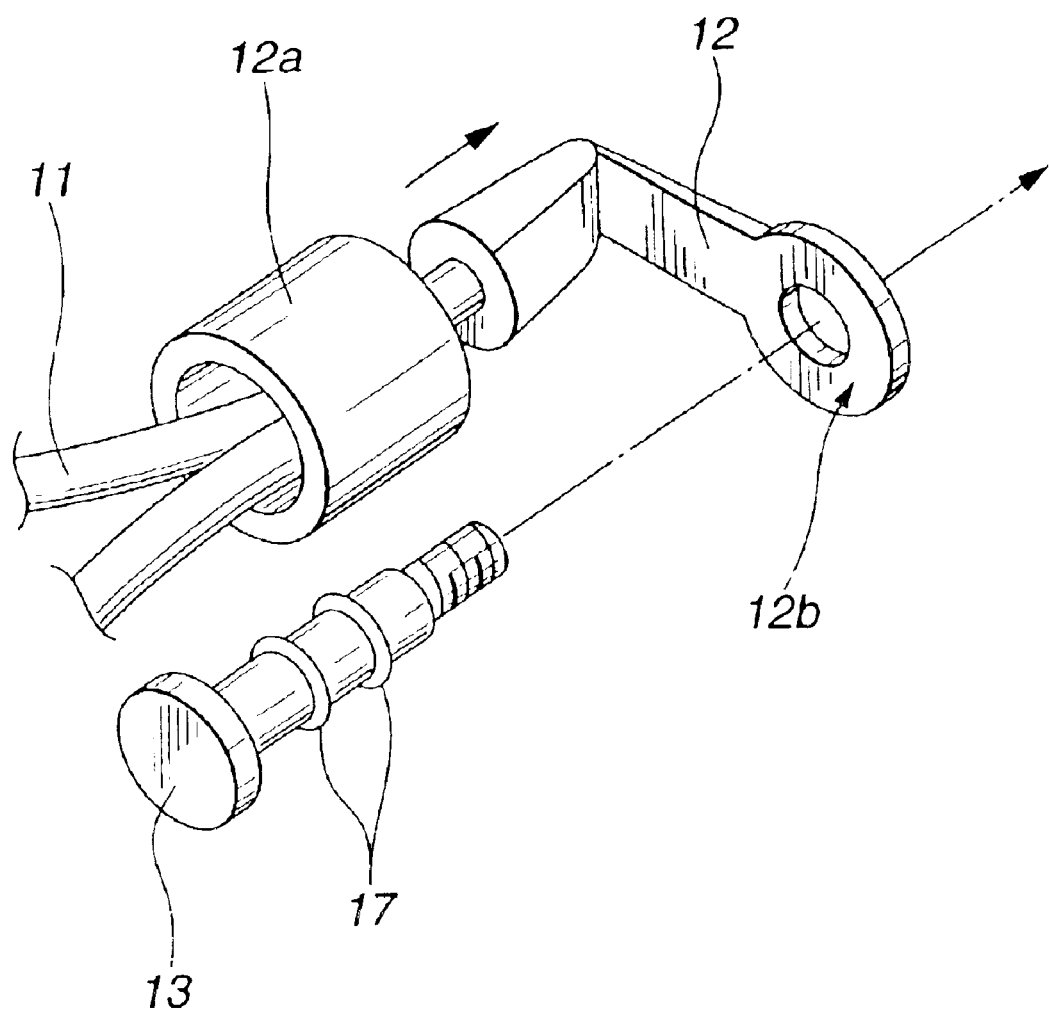

Referring now to FIG. 4, an assembling method in the neighborhood of the terminal 12 will be described. The terminal 12 is formed by bending a metallic plate, and by covering a part of the terminal 12, to which the electric wire 11 is joined with solder 1 with a heat-shrinkable tube 12a for insulation. The other end of the terminal 12, to which the electric wire 11 is not joined with solder, has a terminal hole 12b. An electrode 13 is passed through the terminal hole 12b, and, as shown in FIG. 2, through a hole 15 made in a partition member 14, and then a nut 16 is screwed onto a corresponding screw part of the electrode 13. As a result, the terminal 12 and the electrode 13 are fastened with respect to the partition member 14. The electrode 13 is provided with an O-ring 17 to maintain airtightness, as shown in FIG. 4.

As shown in FIGS. 2 and 3, an electric wire 20, exposed by peeling the coating from the cord 4, is fixed to the electrode 13 with solder, and the coating edge of the cord 4 is fixed by a stop ring 22 inside a heat-shrinkable tube 21. Thereby, the cord 4 is prevented from being carelessly detached from the vibrator body 3.

A connecting member 26 provided with O-rings 24 and 25 in pairs, for maintaining airtightness beforehand is bonded to a casing 23 in which the transducer 10 is incorporated. A rubber plate 29 is stuck onto a side face of a flange 27 of the transducer 10, which faces the terminal 12, by means of an adhesive or the like. The rubber plate 29 stuck onto the flange 27 corresponding to a nodal position can be removed because heat or vibrations are seldom generated.

A set of the transducer 10, nut 16, partition member 14, electrode 13, terminal 12, and electric wire 11 is inserted into the casing 23 from the side of the screw part 28 of the open end of the casing 23. Then, the partition member 14 is inserted to be fit in the hole 30 of the connecting member 26. The hole 30 having a width-across-flat part 31 engages with a partition member 14a, thereby preventing the partition member 14 from rotating carelessly.

Thereafter, a packing 32 for securing airtightness is sandwiched between the partition member 14 and the connecting member 26, the partition member 14 is then hung on an airtightness confirmation hole 33 by the use of a jig (not shown) and is withdrawn into the width-across-flat part 31, and the screw part of the partition member 14 is fixed with a nut 34. In order to fix the transducer 10 to the casing 23, a packing 36 and a washer 37 for preventing the slippage of the packing are inserted from the side of a horn 35 that increases amplitude, and a fixing member 38 is screwed into the screw part 28.

Airtightness of the inside with respect to the outside is secured by O-rings 39 and 40, which are fastened to the fixing member 38 beforehand, and the packing 36. When inspecting the airtightness, an airtightness confirmation connector is attached to the airtightness confirmation hole 33, and compressed air is sent in water, thus detecting the presence of bubbles. After the inspection is completed, an airtight cap 42 with an O-ring 41 is screwed for maintaining the airtightness. Thereafter, the nut 16 and the electrode 13 are completely sealed up with a sealing agent 43 for the prevention of a short circuit.

The cord 4 is beforehand passed through an inner cap 51, an outer cap 52, and an O-ring 53. The inner cap 51 with an O-ring 54 is screwed to the connecting member 26. The outer cap 52 is then attached to the outer periphery of the connecting member 26. Thereafter, a breakage prevention member 55 is screwed in the inner cap 51 so as to prevent the cord 4 from breaking, and thus the vibrator body 3 is completed. The O-ring 25 and the O-ring 54 prevent water from entering a gap between the inner cap 51 and the connecting member 26. The O-ring 53 prevents water from flowing from a gap between the cord 4 and the inner cap 51.

Figure 5:
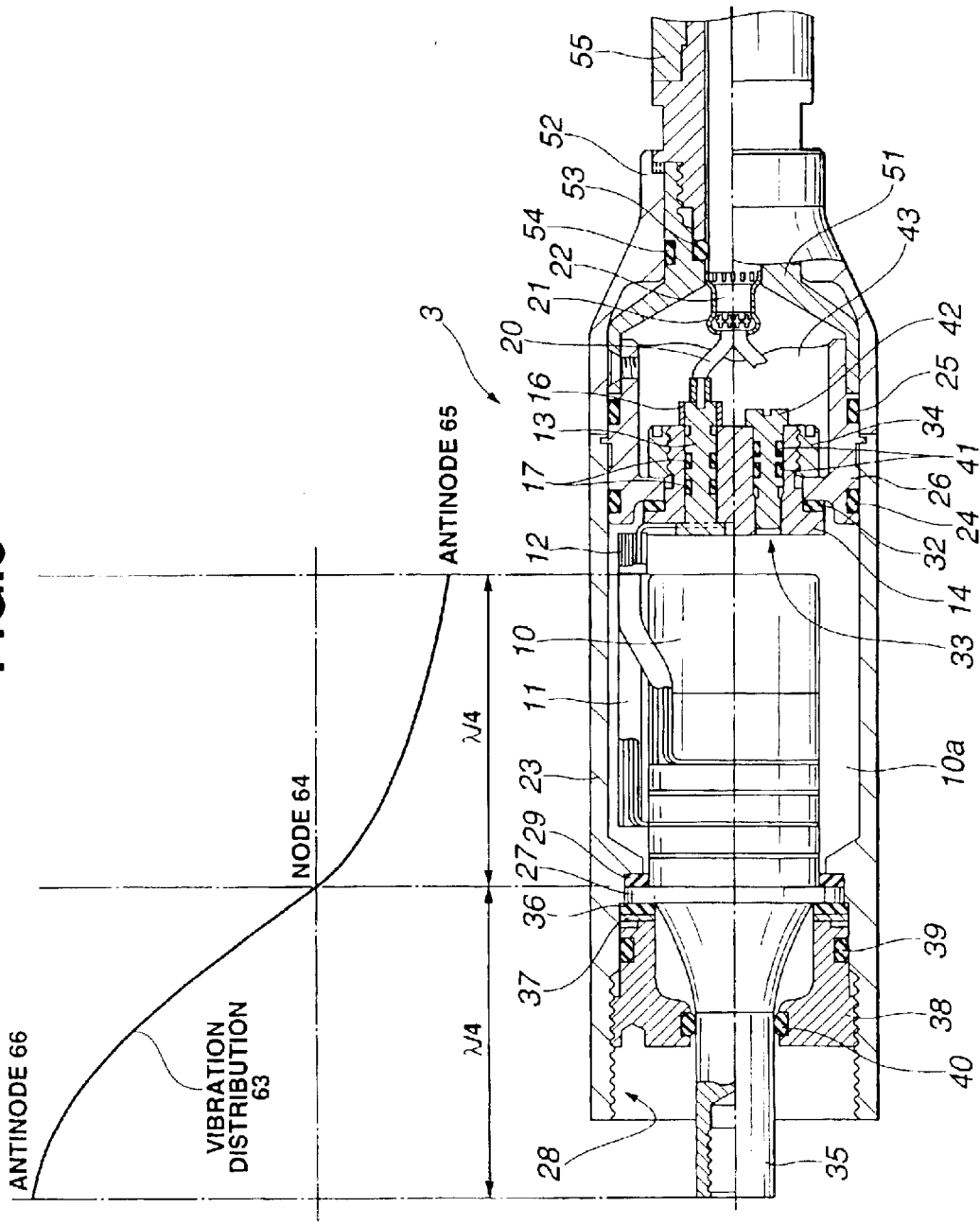

FIG. 5 shows the positional relationship between a vibration distribution 63 and the inside of the vibrator body 3. A node 64 of the vibration is located at the flange 27, an antinode 66 of the vibration is located at the top of the horn 35, and an antinode 65 of the vibration is located at the rear end of the transducer 10. Each antinode of the vibration coincides with a position of a ¼ wavelength of the node 64.

Operation

After the ultrasonic vibrator 1 is used as the vibrator of an ultrasonic coagulotomy instrument during surgery, the ultrasonic vibrator 1 is disconnected from the instrument and, with the waterproof cap 5 on the plug 2, is flushed to wash away dirt, such as body fluids, therefrom. After washing, the ultrasonic vibrator 1 is put into an autoclave sterilization device.

In the autoclave sterilization device, a pre-sterilizing step is performed in which air in the device is withdrawn therefrom, and negative pressure is applied. Thereafter, a sterilizing step is performed in which a high-pressure steam is injected. As a result, the vibrator is sterilized. Normally, the vibrator is taken out of the autoclave sterilization device after the drying step subsequent to the sterilizing step. However, if sterilization is urgently needed during surgery, the drying step of is occasionally omitted.

If the drying step is omitted, it is impossible to completely remove water resulting from a steam that has entered the inside of the vibrator body 3 through the inside of the cord 4 from the coating of the cord 4 and the plug 2.

However, the connecting member 26 and the partition member 14 are used as barrier members that make up the inside of the vibrator body 3. In addition, O-rings 17 and 41 are mounted on the packing 32, the electrode 13, and the airtight cap 42. These prevent water from entering a lumen 10a (see FIG. 3) of the transducer 10. In addition, the sealing agent 43, by which the electrode 13 is sealed and insulated, prevents a short circuit.

Effect

As mentioned above, in this embodiment, it is possible to normally use the vibrator during surgery without causing an oscillatory disorder of the vibrator and avoid the extension of surgery time, for example, because water is prevented from entering the lumen 10a of the transducer 10 even if the autoclave sterilization in which the drying step is omitted is urgently performed during surgery, or the autoclave sterilization without the drying step is performed in a hospital having only an autoclave sterilization device that originally does not perform a drying step.

No problem occurs even if each of the O-rings for maintaining airtightness is used as a pair of O-rings, in order to improve the airtightness.

Embodiment 2

Since a second embodiment is almost the same as the first embodiment, different points alone will be described. The same reference characters are respectively given to the same constituents as in the first embodiment, and a description of them is omitted.

Structure

Figure 6:
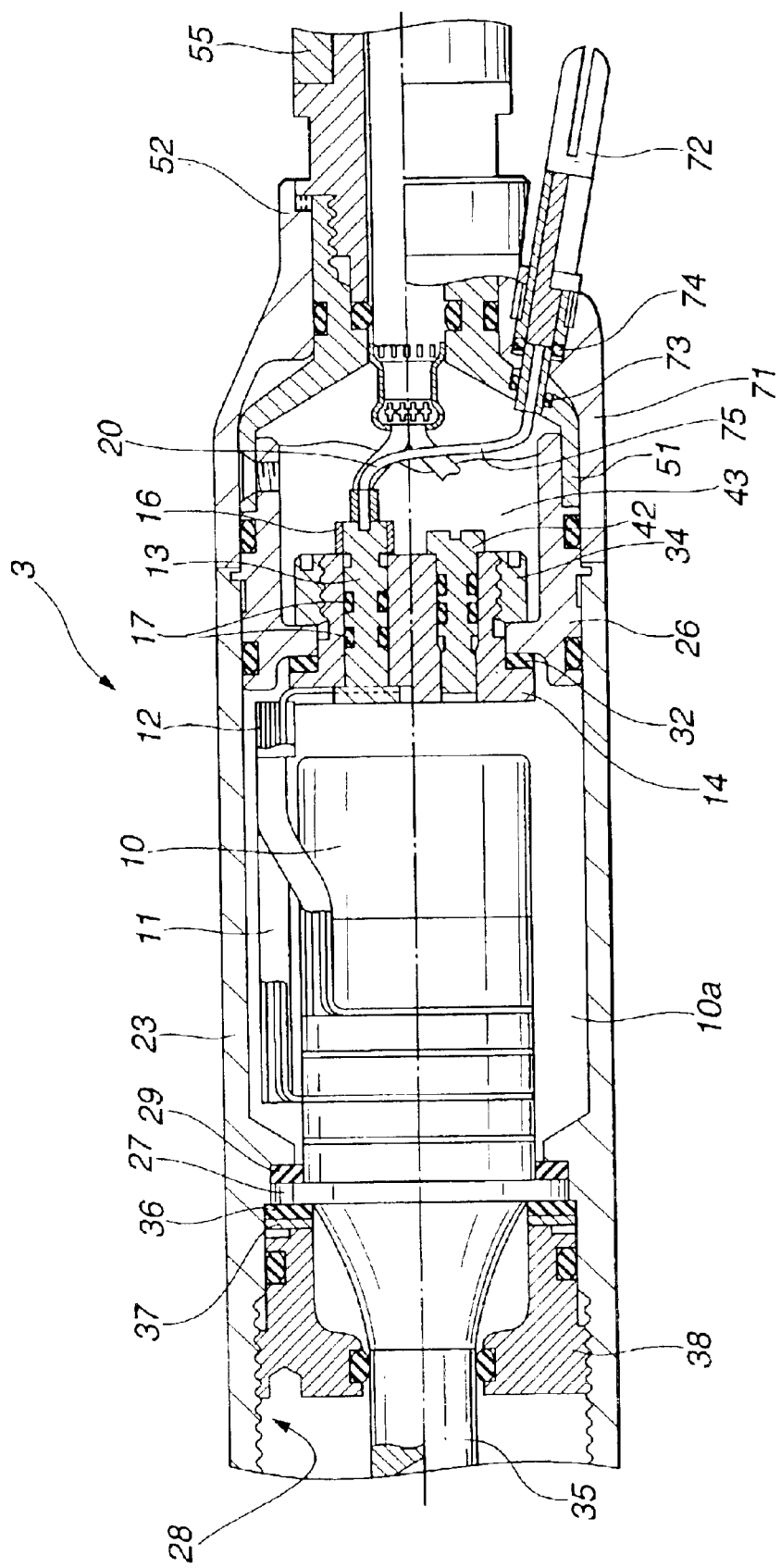
FIG. 6 is an axially sectional view of a vibrator body according to a second embodiment of the present invention.

In a vibrator body 3 in this embodiment, the outer cap 8 in the first embodiment is replaced by an outer cap 71 provided with a terminal portion 72 for connecting an electric connection cord, as shown in FIG. 6. The terminal portion 72 is screwed on the outer cap 71, and watertightness is kept by O-rings 73 and 74. An end of an electric wire 75 is joined to an internal end of the terminal portion 72 with solder, and the other end of the wire 75 is joined to the electrode 13 with solder. The remainder of the structure is the same as in the first embodiment.

Operation

In this embodiment, an electric knife can be used by connecting an electric-knife connecting cord to the terminal portion 72 when using the ultrasonic coagulotomy instrument. The remainder of the operation is the same as in the first embodiment.

Effect

According to this embodiment, all that is required to use the electric surgical knife is to connect the connecting cord to the terminal portion 72 of the vibrator, without using a probe for the knife, in a surgical operation, especially, in an endoscopic surgical operation. Therefore, in addition to the results achieved in the first embodiment, another result can be obtained in that there is no need to exchange devices during surgery, thus allowing a surgeon to operate without such difficulties.

As in the first embodiment, no problem occurs even if each of the O-rings for maintaining airtightness is used as a pair of O-rings, in order to improve the airtightness.

Embodiment 3

Since a third embodiment is almost the same as the first embodiment, different points alone will be described. The same reference characters are respectively given to the same constituents as in the first embodiment, and a description of them is omitted.

Structure

Figure 7:
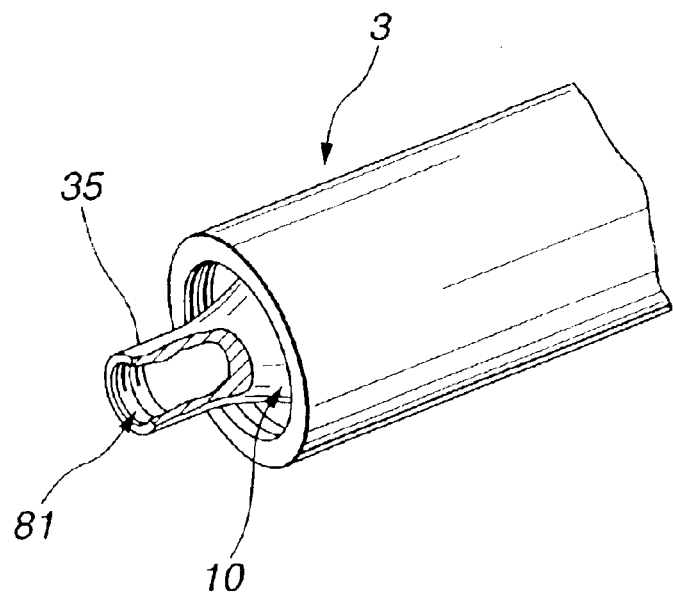
FIGS. 7 to 11 show a third embodiment of the present invention.
Figure 8:
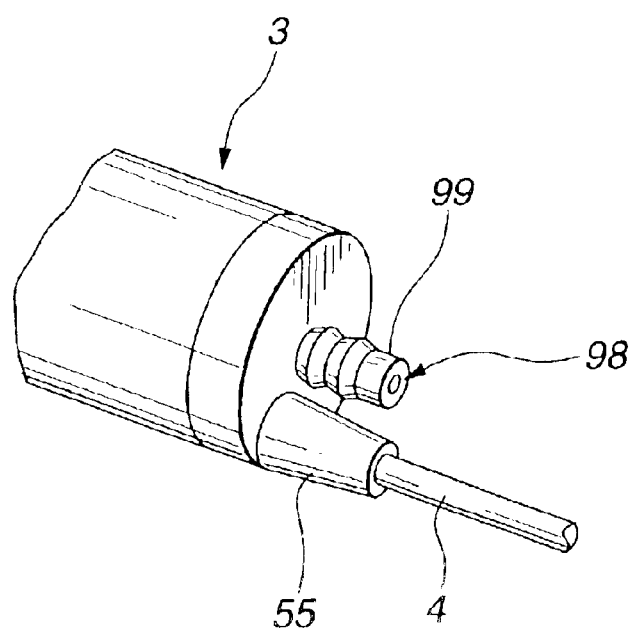

In a vibrator body 3 in this embodiment, a horn 35 for increasing the amplitude/vibration of the transducer 10 has a through hole 81 extending along the axial center line of the vibrator body 3, as shown in FIG. 7. And, as shown in FIG. 8, the member of the horn 35 is constructed as the same constituent as a tubular member 82 that extends to the rear end of the transducer 10. The through hole 81 is a duct coaxial with a suction duct 98 which is a through hole of a tubular mouthpiece 99 disposed at the rear end of the vibrator body 3.

Figure 9:
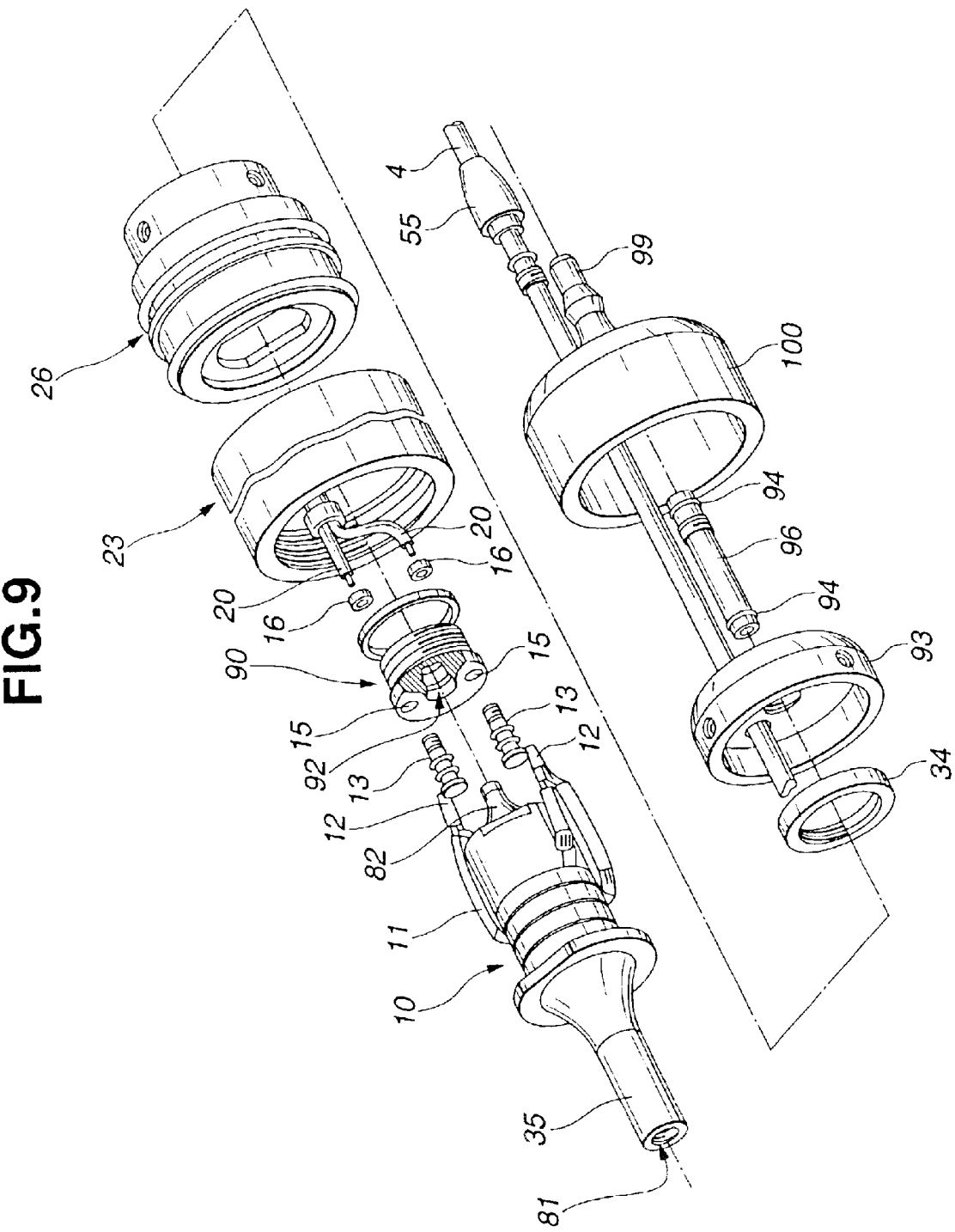

The structure of the vibrator body 3 in this embodiment will be described hereinafter with reference to FIGS. 9 and 10.

A through hole 92 with an O-ring 91 is made in the center of a partition member 90 in this embodiment instead of the partition member 14 shown in the first embodiment. A tubular member 82 is inserted in the through hole 92.

In this state, a nut 16, an electrode 13, a transducer 10, and a partition member 90 are inserted into the inside of a casing 23, as in the first embodiment, and are fastened by a nut 34. An inner cap 93 in this embodiment is fastened to a connecting member 26 by means of a screw (not shown) instead of the inner cap 51 in the first embodiment. A pipe 96 having a tubular duct 95 provided with an O-ring 94 is then screwed on the inner cap 93, and is fixedly inserted into the through hole 92 of the partition member 90. The suction mouthpiece 99 having the suction duct 98 provided with an O-ring 97 is screwed onto an outer cap 100 in this embodiment instead of the outer cap 52 in the first embodiment, and the outer cap 100 is fastened to the connecting member 26. The cord 4 and the breakage prevention member 55 are screwed and fixed at an eccentric position with respect to the outer cap 100. The other structure is the same as in the first embodiment.

Operation

In addition to the operation in the first embodiment, in this embodiment, the vibrator body 3 has the through hole, and, accordingly, when a suction tube (not shown), which is combined with an outside suction apparatus, is connected to the suction mouthpiece 99, a liquid absorbed from the tip of a perforated probe (not shown) of the horn 35 can flow to the suction tube via the through hole 81, the pipe 96, and the suction duct 98, and can drain into the outside. Alternatively, when a tube for supplying water is attached to the suction mouthpiece 99, physiological saline, for example, can flow to the tip of the perforated probe (not shown) through the suction duct 98, the pipe 96, and the through hole 81, and thus can be supplied to a surgical region.

Effect

According to this embodiment, the same effect as in the first embodiment can be obtained even if the vibrator is used as a vibrator unit of the ultrasonic suction apparatus. The ultrasonic suction apparatus can suck vital tissues in the form of emulsion and can suck peripheral tissues while leaving vessels in accordance with the function of selectiveness of tissues, and therefore time the required for surgery can be shortened. In addition, since physiological saline etc. can be supplied to a surgical region when necessary, surgery can be performed smoothly.

Figure 10:
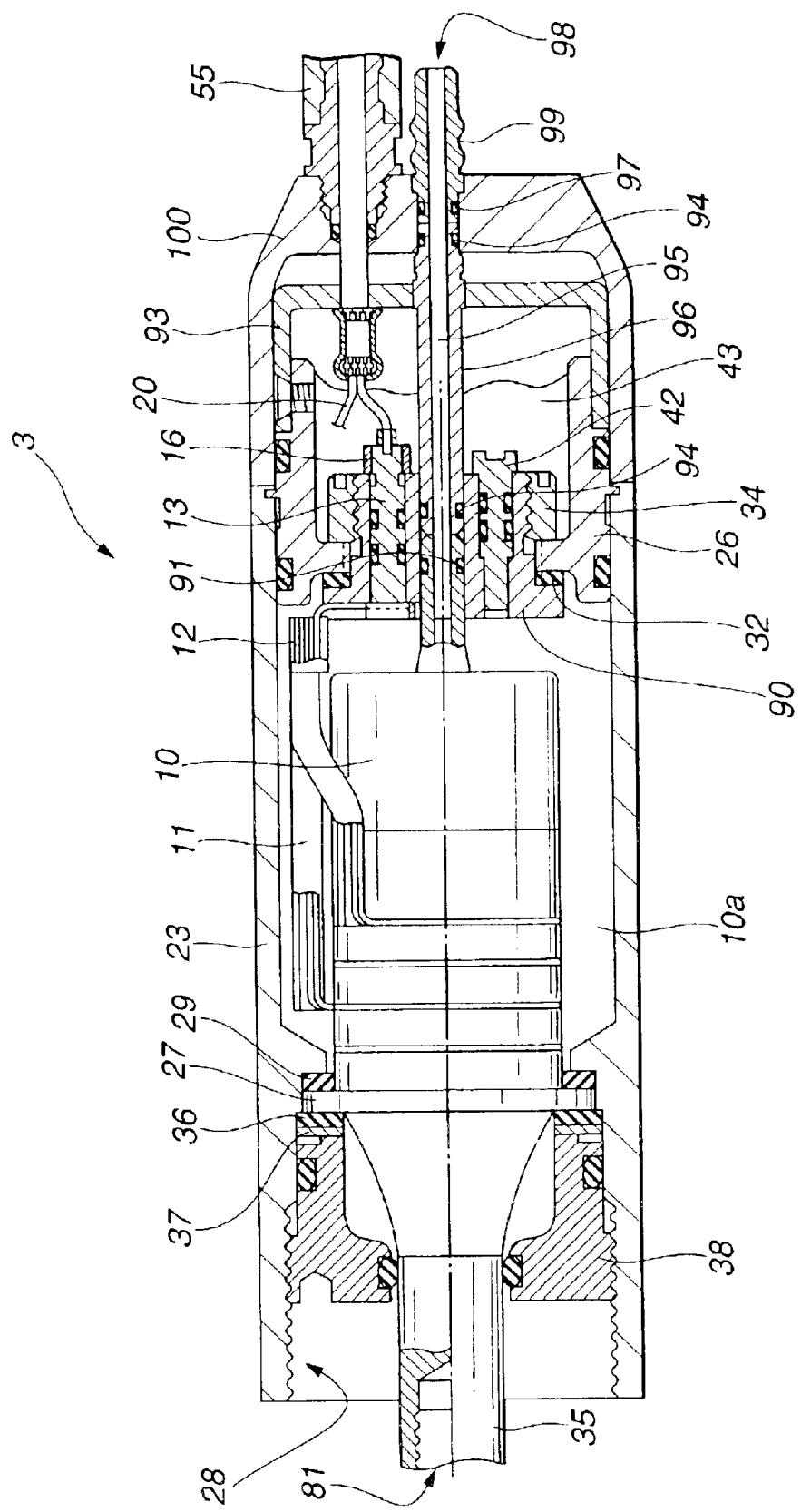
Figure 11:
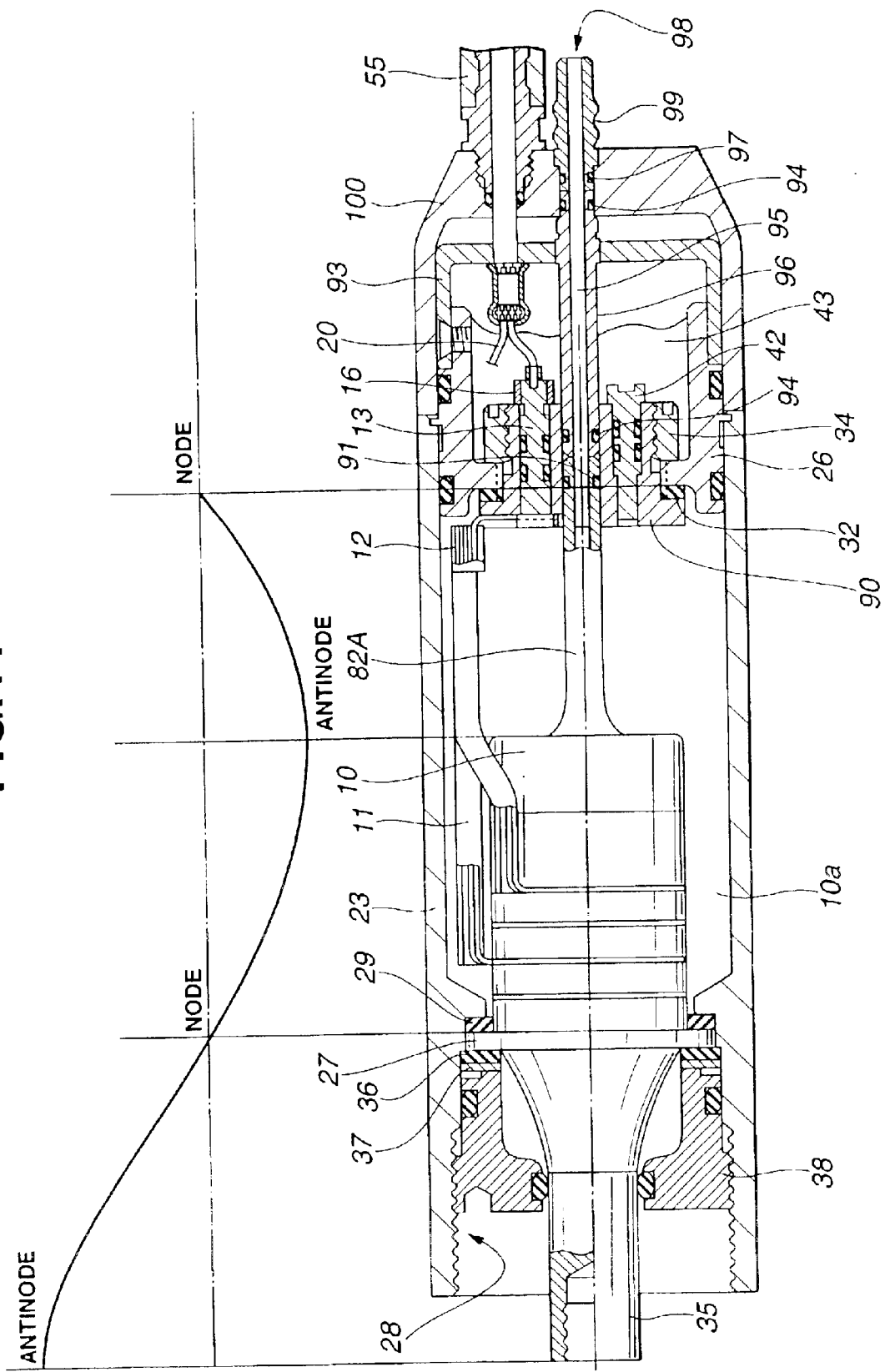

A modification of the vibrator body 3 shown in FIG. 10 can be performed as shown in FIG. 11. A feature different from that of FIG. 10 is that the O-ring 91 for maintaining airtightness is situated at the nodal position of the vibration as a member 82A extending the tubular member 82. As a result, frictional heat caused by vibrations is not easily generated because of the nodal position of the vibration even if ultrasonic oscillation occurs, and the rise of temperature is suppressed.

As in the first embodiment, no problem occurs even if each of the O-rings for maintaining airtightness is used as a pair of O-rings, in order to improve the airtightness.

Embodiment 4

Figure 17:
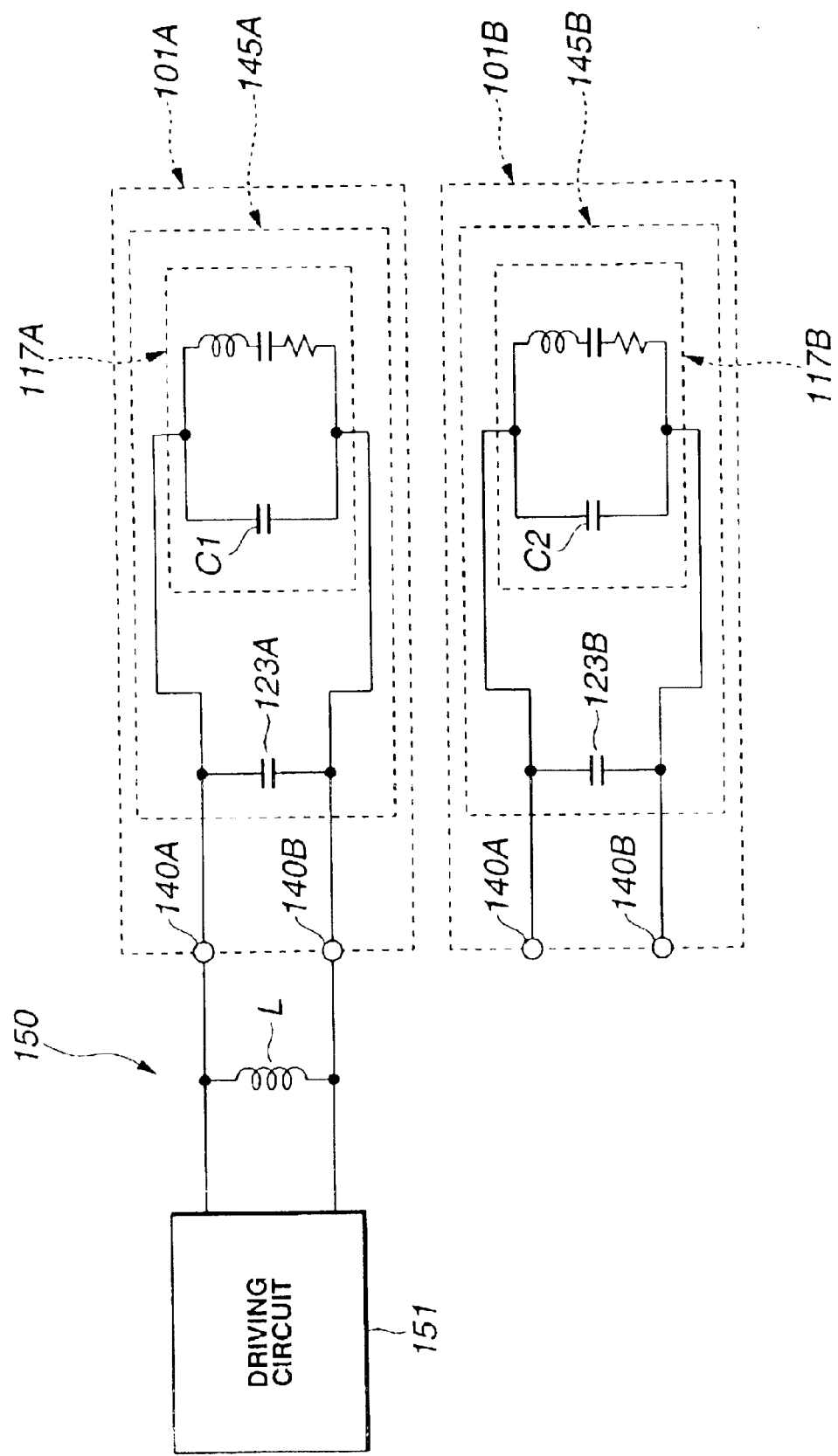

FIG. 17 schematically shows the structure of the main part of an electric circuit of an ultrasonic treatment apparatus. AS shown in the figure, either an ultrasonic vibrator unit 101A or 101B according to a fourth embodiment of the present invention is connected to a main body (i.e., driving power-supply unit) 150 of the ultrasonic treatment apparatus through connecting pins 140A and 140B of a plug 103, described later (see FIG. 12).

The ultrasonic vibrator unit 101A (101B) is provided with a transducer 117A (117B) having a braking capacitor (braking capacitive component) C1 (C2). A capacitor (capacitive component) 123A (123B) is connected in parallel with the transducer 117A (117B).

The main body 150 of the ultrasonic treatment apparatus is provided with a driving circuit 151. The driving circuit 151 that is connected to the connecting pins 140A and 140B of the plug 103 drives the transducer 117A (117B) of the ultrasonic vibrator unit 101A (1B) connected to the main body 150 at the mechanical resonance point thereof.

An inductor (inductive component) L is mounted in the main body 150 of the ultrasonic treatment apparatus. The inductor L is placed between the connecting pins 140A and 140B, and is arranged to be connected in parallel with the transducer 117A (117B) of the ultrasonic vibrator unit 101A (101B) connected to the main body 150. The inductor L is provided to offset a composite capacitance value (i.e., sum of capacity susceptance) between the braking capacitor C1 (C2) and the capacitor 123A (123B) in the ultrasonic vibrator unit 101A (101B).

The capacitor 123A (123B) as the capacitive component is provided to keep the composite capacitance value in the ultrasonic vibrator unit 101A (101B) constant and to equalize the composite capacitance value with the inductance of the inductor L. In other words, the capacitor 123A (123B) functions to compensate the size of the capacity susceptance of the braking capacitor C1 (C2) which depends on the kind of the transducer 117A (117B).

In this embodiment, when the ultrasonic vibrator unit 101A is connected to the main body 150, the driving circuit 151 and the transducer 117A are connected to each other through the connecting pins 140A and 140B. Additionally, the inductor L, the braking capacitor C1, and the capacitor 123A are connected in parallel with each other through the connecting pins 140A and 140B. This connection makes it possible to offset a composite capacitance value between the braking capacitor C1 and the capacitor 123A by the inductance of the inductor L. That is, the composite capacitance value therebetween is equalized with the inductance of the inductor L. As a result, the capacity susceptance of the braking capacitor C1 of the transducer 117A is infallibly offset. Accordingly, the transducer 117A of the ultrasonic vibrator unit 101A can be reliably driven at the mechanical resonance point thereof. Therefore, surgical operations, such as destruction of a calculus or removal of a tumor, can be efficiently performed by the ultrasonic vibrator unit 101A.

Even if the ultrasonic vibrator unit 1B is connected to the main body 150, the composite capacitance value will be offset by the inductance of the inductor L.

As described above, in this embodiment, the difference in the size of the capacity susceptance of the braking capacitor, which various types of transducers individually have, is designed to be offset by the capacitor 123A (123B). That is, even if the transducers of the ultrasonic vibrator units connected to the main body 150 are different in kind from each other, the composite capacitance value thereof is designed to be kept constant. Therefore, even when transducers that are different in the size of the capacity susceptance of the braking capacitor are driven, the capacity susceptance of the braking capacitor can be infallibly offset by one kind of inductor. As a result, various types of transducers can be reliably driven at the mechanical resonance point thereof.

The mechanical structure of the ultrasonic vibrator unit 101A (101B) is shown in FIGS. 12 to 16.

Figure 12:
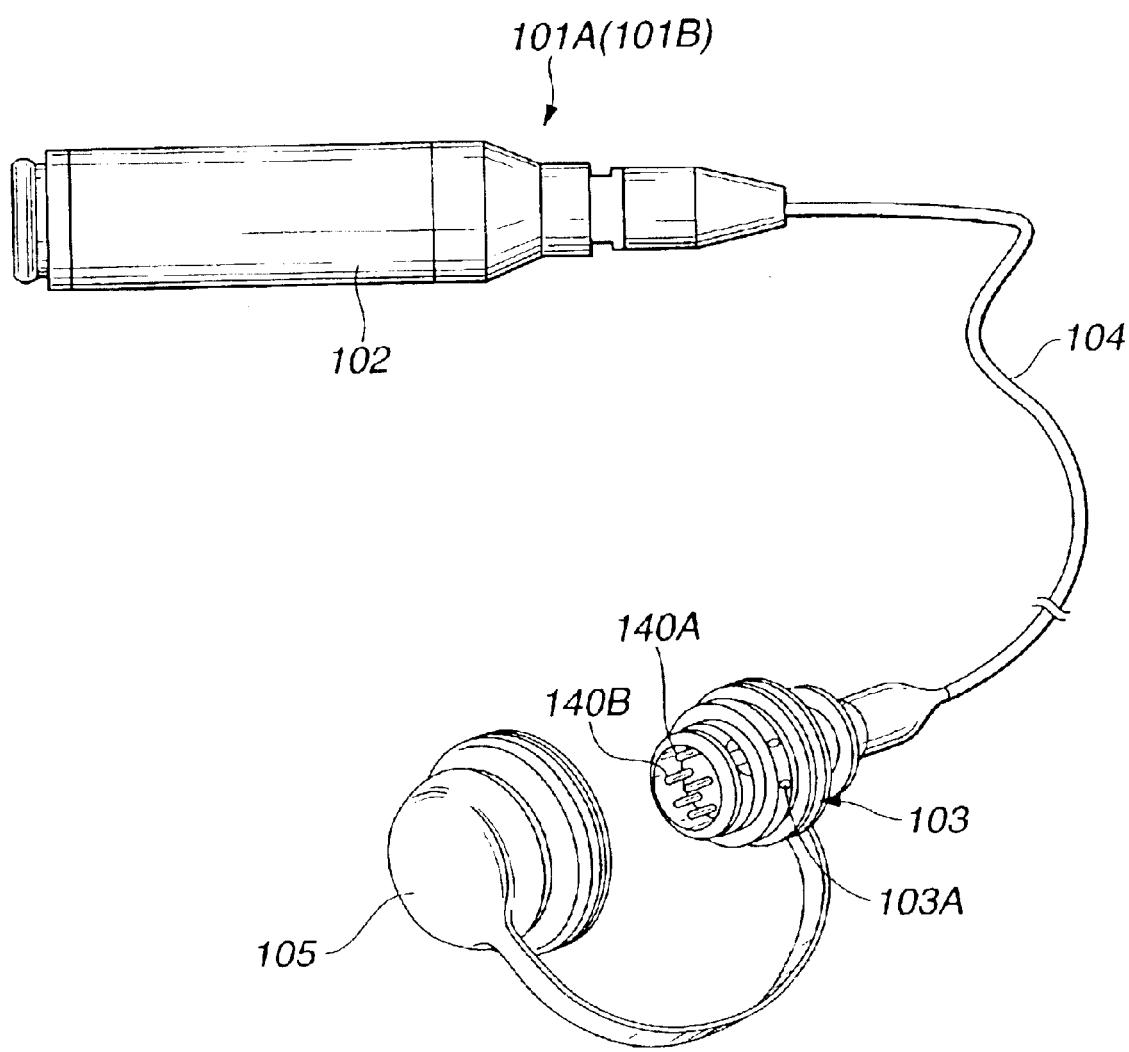
FIGS. 12 to 22 show a fourth embodiment of the present invention.

Referring to FIG. 12, a handpiece cord 104 extends from the base end of the vibrator unit 101A (101B), and a plug 103 is joined to the end of the handpiece cord 104. The plug 103 has connecting pins 140A and 140B which are to be electrically connected to a connector (not shown) of the main body 150 of the ultrasonic treatment apparatus. A rib 103A projects from the outer surface of the plug 103. The rib 103A is engaged with the connector of the main body 150 and serves as an indicator for determining the direction in which the plug 103 is connected to the main body 150. The plug 103 additionally has a watertight cap 105 for maintaining watertightness when not used.

Figure 13:
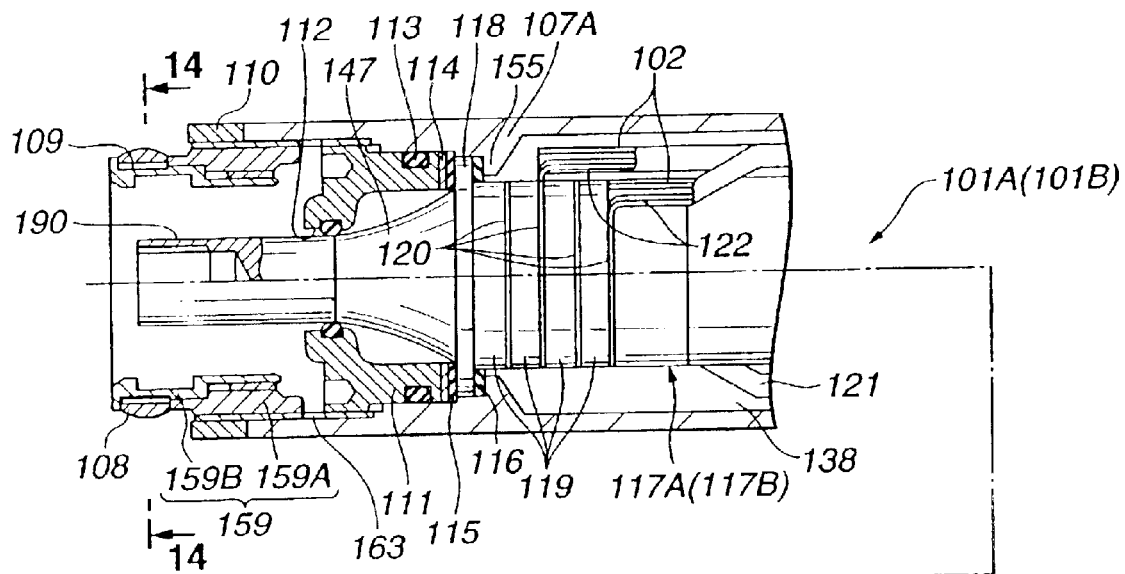
Figure 13:
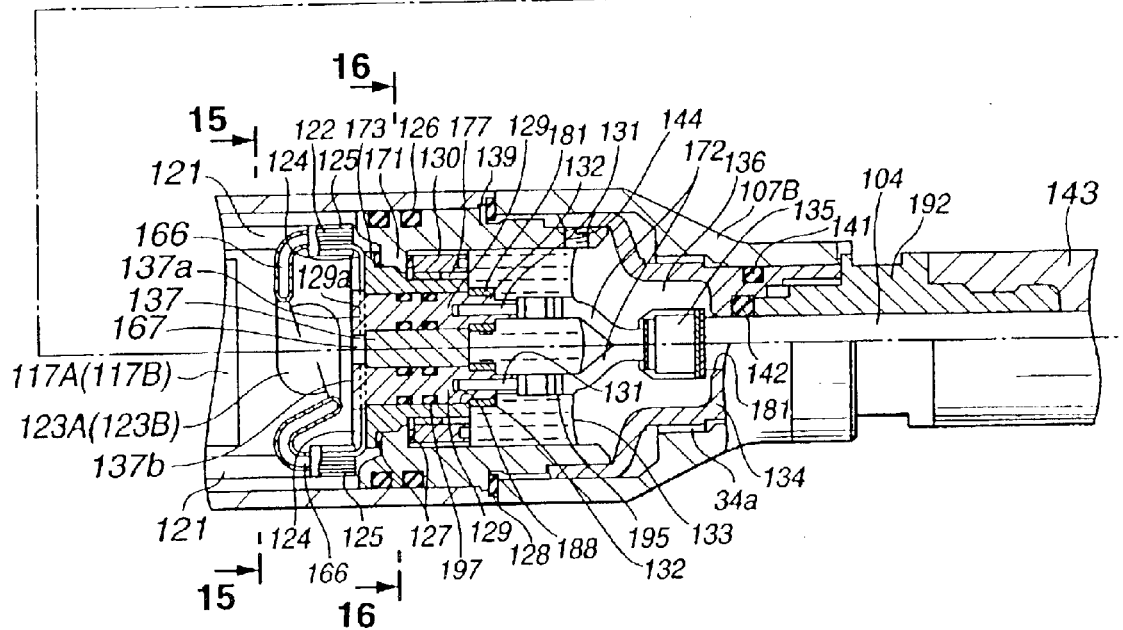
Figure 14:
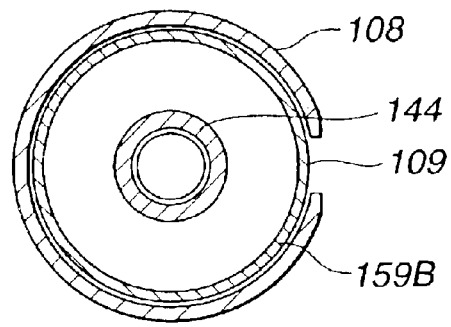
Figure 15:
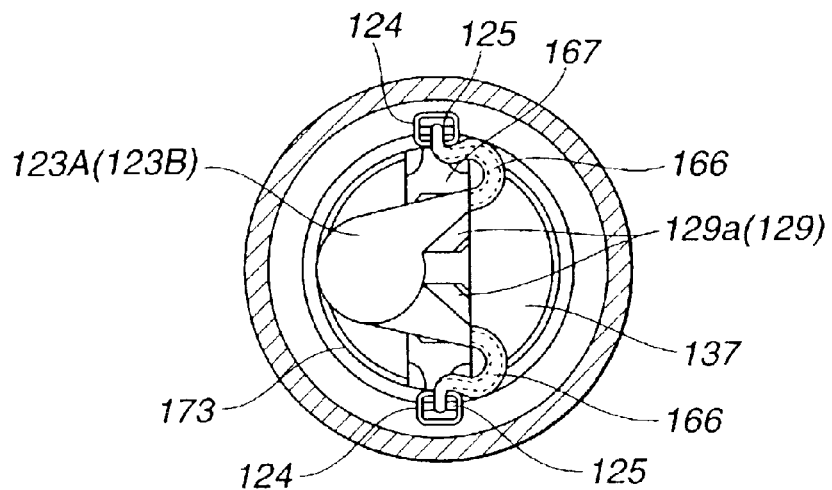
Figure 16:
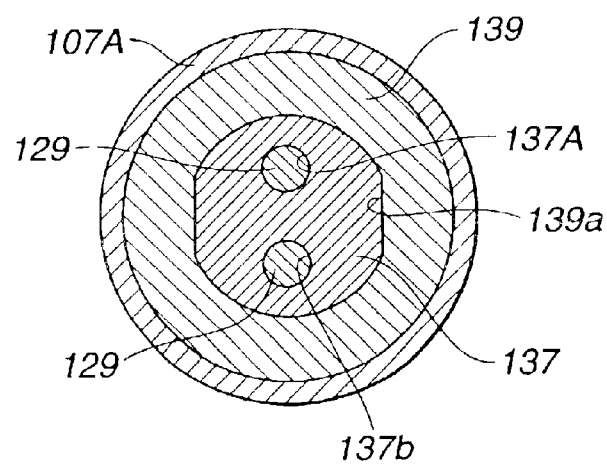

As shown in FIG. 13, the vibrator unit 101A (101B) is constructed as a handpiece 102. The handpiece 102 has a cylindrical cover used as a handgrip. The cover consists of a front case 107A and a rear case 107B, each detachable. The front case 107A includes a transducer unit 145A (145B) constructed by integrally assembling the transducer 117A (117B) and the capacitor 123A (123B). (See FIGS. 17 and 18 in addition to FIG. 13).

The transducer 117A (117B) has a vibrator body including a plurality of piezoelectric elements 119, and a horn 147, connected to the vibrator body, for amplifying an ultrasonic vibration generated in the vibrator body and increasing the amplitude. The tip of the horn 147 has a female screw 190 to which a probe unit, not shown, is fastened. A flange 118 projects from the base of the horn 47.

The transducer unit 145A (145B) is supported inside the front case 107A by means of a supporting nut 111 screwed into the top of the front case 107A. Specifically, the transducer unit 145A (145B) is supported inside the front case 107A such that the flange 118 of the horn 147 is sandwiched between a supporting portion 155 projecting from the inner surface of the front case 107A and the supporting nut 111. In this embodiment, a first supporting rubber 116 for absorbing vibrations is placed between the supporting portion 155 and the flange 118. Additionally, a second supporting rubber 115 and a washer 114 that serve to absorb vibrations and maintain watertightness and airtightness are placed between the flange 118 and the supporting nut 111.

A cylindrical connection member 159A is screwed in a screw portion 163 formed in the inner surface of the top of the front case 107A, and a cylindrical receiving member 159B is screwed in the inner surface of the connection member 159A. These members 159A and 159B make up a connection portion 159 that connects the vibrator unit 101A (101B) to a handle unit, not shown. Specifically, an engagement ring 108 (see FIG. 14) that was a C-shaped section is disposed in an annular groove 109 formed on the receiving member 159B, and the engagement ring 108 is elastically engaged with an engagement groove of the handle unit, and thereby the vibrator unit 101A (101B) is connected to the handle unit.

An adjusting nut 110 is screwed on the outer surface of the connection member 159A screwed to the screw portion 163 of the front case 107A, with the adjusting nut 110 in contact with the top of the front case 107A. When the adjusting nut 110 is rotated, the connection member 159A is axially moved with respect to the front case 107A, and the axial position of the connection portion 159 is adjusted.

An O-ring 112 is interposed between the supporting nut 111 and the horn 147. The O-ring 112 that secures watertightness and airtightness supports and positions the horn 147 at the center of the front case 107A. Additionally, an O-ring 113 that secures watertightness and airtightness is interposed between the supporting nut 111 and the front case 107A.

Each of the piezoelectric elements 119 that is a constituent of the vibrator body is arranged to be interposed between electrode plates 120 and 120. An electric wire 122 for supplying a current is united to the electrode plate 120 with solder. In this embodiment, when a current is caused to flow between the electrode plates 120 through the electric wire 122, the piezoelectric element 119 expands and contracts, thus generating ultrasonic vibrations.

The electric wire 122 extends to the inside of a second heat shrinkable tube 125 located on the base end side of the front case 107A through a first heat shrinkable, electrically nonconductive tube 121. Legs 166, 166 of the capacitor 123A (123B) disposed on the base end side of the transducer 117A (117B) extend to the inside of the second heat shrinkable tube 125, and are soldered to terminals 124, 124, respectively, together with the electric wire 122.

The cylindrical connection member 139 is fitted in the inner surface of the base end of the front case 107A. In this embodiment, an O-ring 126 for securing watertightness and airtightness is interposed between the front case 107A and the connecting member 139. The base end of the connecting member 139 projects from an opening on the base end side of the front case 107A. The top of a cylindrical inner cap 134 is fixed to the base end of the projecting connecting member 139 by means of a screw 144. The rear case 107B is screwed on a screw portion 134a formed in the outer peripheral surface of the inner cap 134 so as to cover the inner cap 134 from the outside. In this embodiment, an O-ring 141 for securing watertightness and airtightness is interposed between the inner cap 134 and the rear case 107B.

In a state where the rear case 107B has been sufficiently screwed on the screw portion 134a as shown in FIG. 13, the top side of the rear case 107B is pressed to be brought in contact with the base side of the front case 107A, with the packing 128 therebetween. The packing 128 is compressed by the pressure of the top side of the rear case 107B and the base side of the front case 107A, thereby securing watertightness and airtightness between the cases 107A and 107B.

The handpiece cord 104 is detachably connected to the base end of the inner cap 134. Specifically, a connection tube 192, fitted on the outer peripheral surface of the base end of the handpiece cord 104, is screwed in the inner cap 134. In this embodiment, an O-ring 142 for securing watertightness and airtightness is interposed between the inner cap 134 and the connection tube 192. A cylindrical breakage prevention member 143 is fixed to the connection tube 192. The breakage prevention member 143 is fit on the peripheral surface of the end of the handpiece cord 104, and prevents breakage of the connected part of the handpiece cord 104.

The end of the handpiece cord 104 extends through the connection tube 192, and projects in the inner cap 134 through an opening 181 of the base end of the inner cap 134. A detachment preventing member 135 whose diameter is larger than the inner diameter of the opening 181 of the inner cap 134 is attached to the end of the handpiece cord 104. Accordingly, the handpiece cord 104 will not come out of the inner cap 134 because the detachment preventing member 135 is bumped against the inner surface of the inner cap 134 when the handpiece cord 104 is carelessly pulled to the operator's side.

A partition 137 by which the handpiece 102 is divided into two watertight/airtight chambers 136,138 is unrotatably attached to the connecting member 139 fitted in the front case 107A. Specifically, as clearly shown in FIG. 16, the partition 137 has a noncircular section, and is inserted into a noncircular fixing hole 139a formed by an inner projection 171 of the top end of the connecting member 139, and thus is incapable of rotating. The partition 137 additionally has a flange 173 on the end of the side facing the capacitor 123A (123B), and has a screw portion 177 on the outer surface of the end projecting to the inner cap 134. A nut 130 is screwed onto the screw portion 177 of the flange, thereby pressing the flange 173 to the inner projection 171, and the partition 137 is fastened to the connecting member 139. In other words, the partition 137 is fastened to the connecting member 139 by sandwiching the inner projection 171 between the flange 173 and the nut 130 screwed on the screw portion 177. Thus, the partition 137 divides the inside of the handpiece 102 into a front chamber 138 of the front case 107A in which the transducer unit 145A (145B) is disposed and a rear chamber 136 of the rear case 107B into which the handpiece cord 104 is drawn. Packings 127, 127 for watertightness and airtightness are each interposed between the nut 130 and the inner projection 171 and between the flange 173 and the inner projection 171.

The partition 137 has two through-holes 137a and 137b. An electrode 129 is passed through each of the through-holes 137a and 137b. The electrode 129 has a rectangular flange 129a on the end of the side facing the capacitor 123A (123B), and has a screw portion 181 on the outer surface of the end projecting to the inner cap 134. A nut 132 is screwed onto the screw portion 181, thereby pressing the flange 129a to the end side of the partition 137, and the electrode 129 is fixed with respect to the partition 137. In other words, the electrode 129 is fixed with respect to the partition 137 by sandwiching the partition 137 between the flange 129a and the nut 132 screwed on the screw portion 181. The electrode 129 is electrically connected to the terminal 124 by sandwiching the terminal 124 between the end side of the flange 129a and the partition 137. The electrode 129 is engaged with a long groove 167 formed in the end side of the partition 137, and is stopped from rotating with respect to the partition 137. O-rings 197 for watertightness and airtightness are each interposed between the electrode 129 and the inner surface of the through-hole 137a, and between the electrode 129 and the inner surface of the through-hole 137b of the partition 137.

Two electric lines 172, 172 are led from the opening of the end of the handpiece cord 104 projecting to the inner cap 134. A pin terminal 131 is electrically connected to the end of the line 172. The pin terminal 131 is subjected to press-fitting and is fixed to terminal connection hole 188 formed in the end of the electrode 129 that projects to the inner cap 134 side. A connected part between the pin terminal 131 and the electric line 172 is coated with a heat shrinkable, electrically nonconductive tube 195.

The rear chamber 136 is almost completely filled with a sealing agent 133. Accordingly, when autoclave sterilization, for example, is performed, high-pressure steam is prevented from entering the front chamber 138 where the transducer unit 145A (145B) is disposed.

Figure 18:
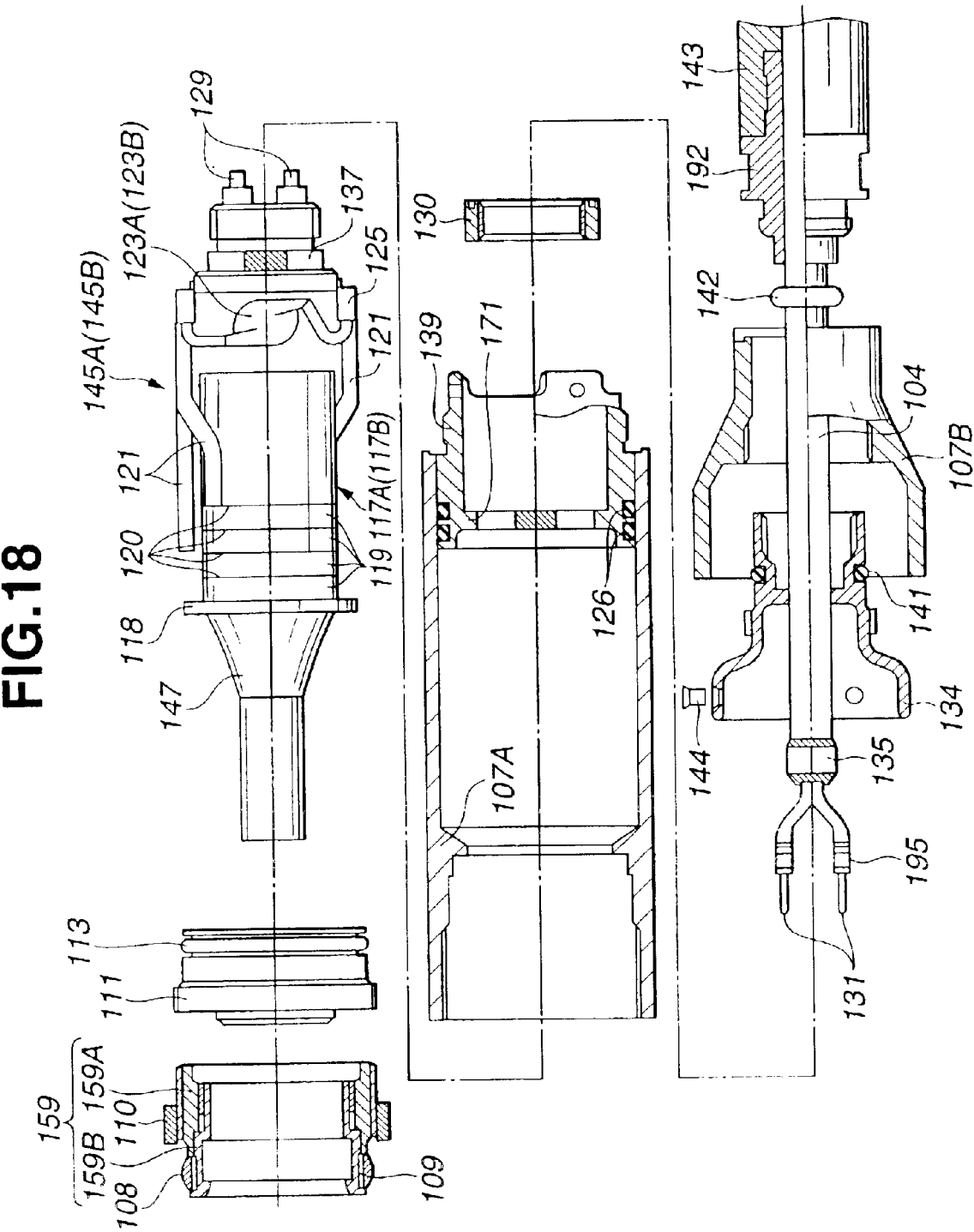

In the thus constructed ultrasonic vibrator units 101A, 101B, the transducer unit 145A (145B) as a single unit can be easily taken out of the handpiece 102 in such a way that the connection portion 159 and the supporting nut 111 are detached from the front case 107A, the rear case 107B and the screw 144 are then detached from the inner cap 134, and the connection between the connecting member 139 and the inner cap 134 is released, and thereby the nut 130 is detached, as shown in FIG. 18.

As mentioned above, in the ultrasonic vibrator units 101A, 101B, the combination of the capacitor 123A (123B) and the transducer 117A (117B), in which matching has been beforehand applied to the main body 150, is constructed as a single unit 145A (145B), and the unit 145A (145B) is arranged to be freely attached to or detached from the handpiece.

Therefore, when either the transducer 117A (117B) or the capacitor 123A (123B) breaks down, there is no need of making a matching adjustment to the main body 150 (i.e., the retrying of matching by e.g. inspection or measurement) if the transducer unit 145A (145B) itself is exchanged. Thus, they can be easily repaired and exchanged.

Figure 19:
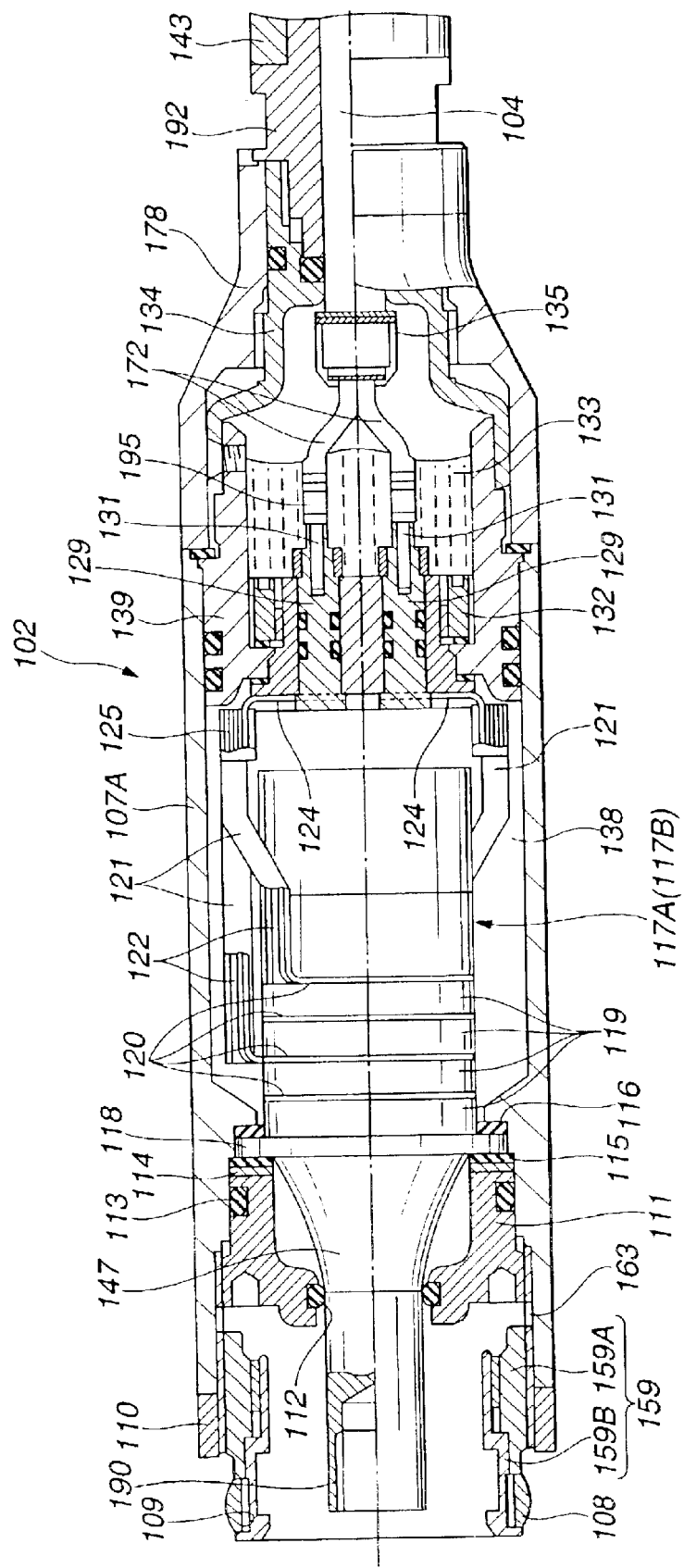
Figure 20:
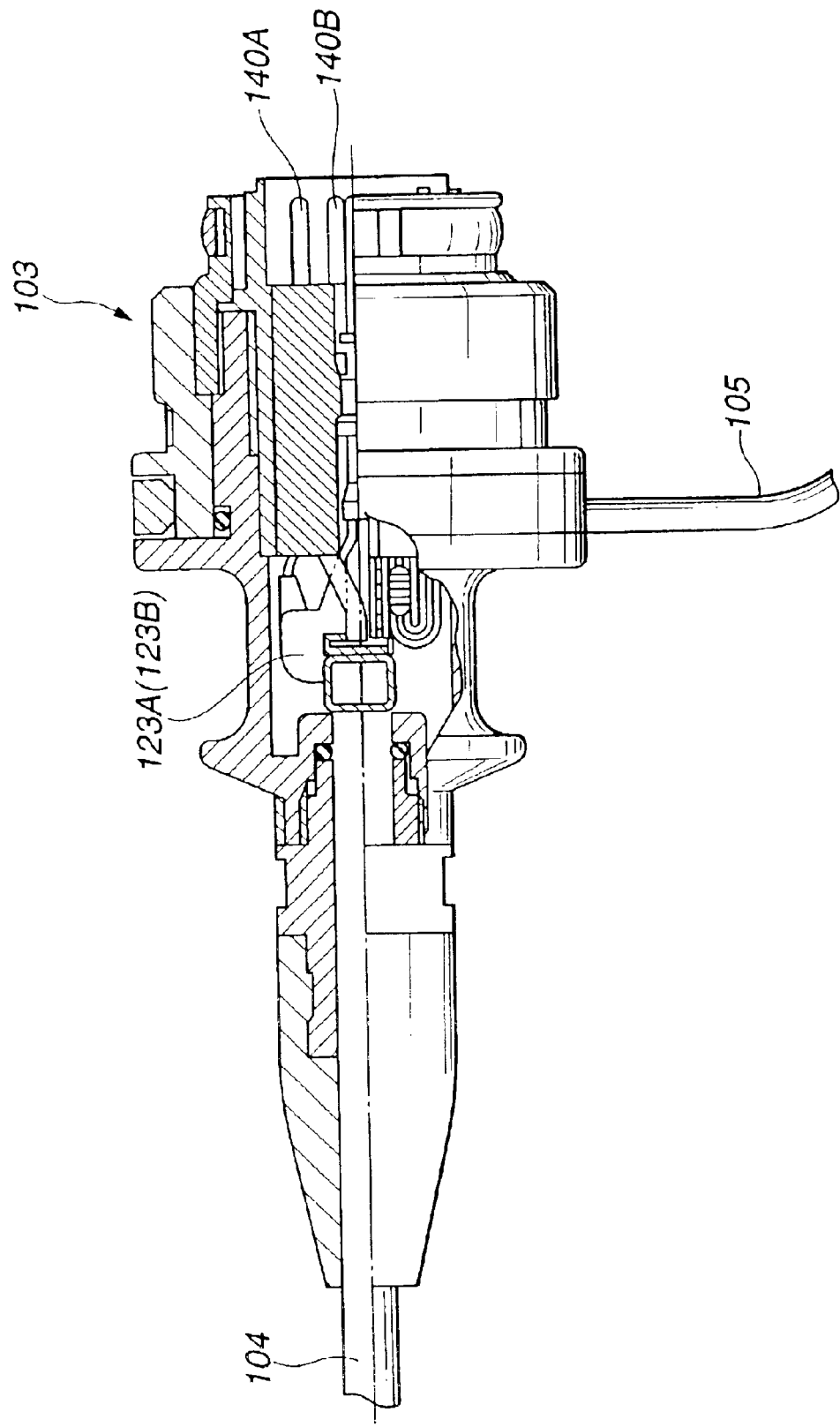
Figure 21:
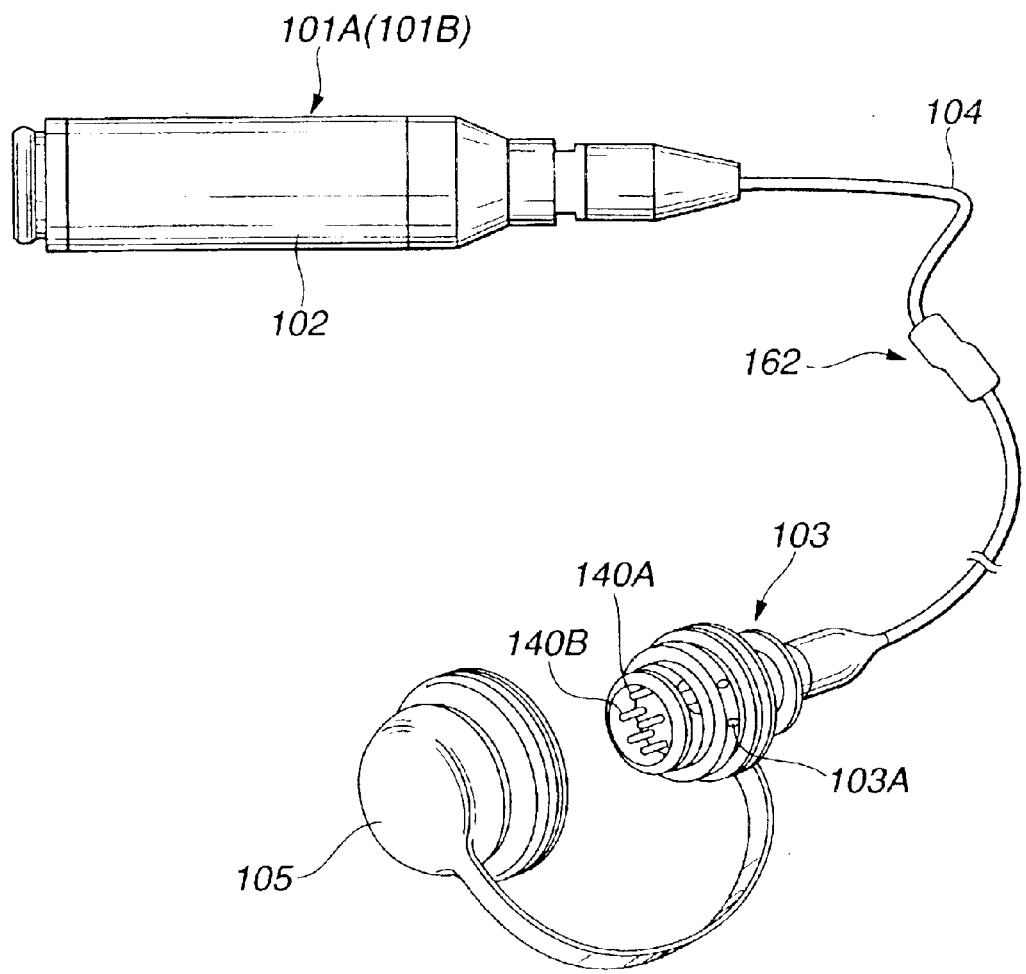
Figure 22:
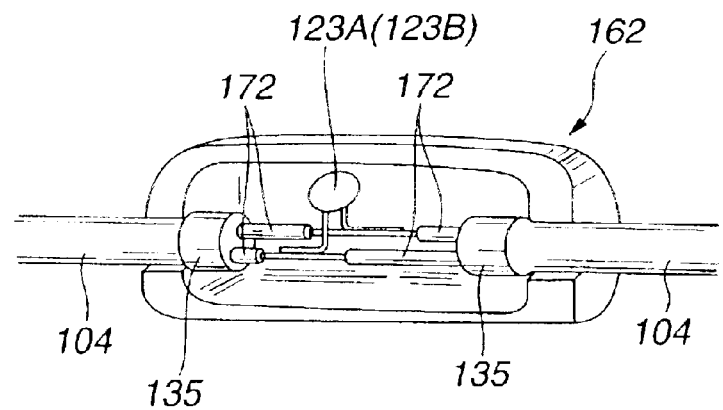

Another example of an embodiment for realizing the size reduction of the handpiece is shown in FIGS. 19 and 20. As shown in FIG. 19, only the transducer 117A (117B) is disposed in the handpiece 102, and, as shown in FIG. 20, the capacitor 123A (123B) is disposed in the plug 103. Therefore, the handpiece can be reduced in size by a space where the capacitor 123A (123B) is disposed. In FIG. 19, the same reference characters are given to the same constituents, respectively, as in the previous embodiments. The size reduction of the handpiece 102 can be realized also by disposing the capacitor 123A (123B) on the way of the handpiece cord 104, as shown in FIGS. 21 and 22. In this structure, the capacitor 123A (123B) is directly connected to the electric line 172 in the handpiece cord 104, and is contained in the case 162. In order to position the case 162, a detachment preventing member 135A that projects in the case 162 is provided in the end of the handpiece cord 104.

In this invention, it is apparent that various embodiments in wide scope can be carried out according to the present invention without departing from the spirit and scope thereof. The present invention is not limited by a specific embodiment thereof, except that it is limited by the attached claims.

What is claimed is:

1. ultrasonic vibrator comprising:

a transducer having a braking capacity component constructed by connecting a plurality of vibrating elements for converting a driving current into vibrations;

a capacitive component portion connected in parallel with said transducer;

a plug detachably connected to an ultrasonic drive generating portion for generating said driving current; and an electric power supply cord for supplying said driving current from said plug to said transducer;

wherein a composite capacity value of said braking capacity component and a capacity component of said capacitive component portion is turned into a capacitive component value that offsets an inductive component disposed in said ultrasonic drive generating portion, and said capacitive component portion is disposed in a cover covering said transducer.

2. The ultrasonic vibrator of claim 1, wherein said transducer and said capacitive component portion are made a single unit.

3. An ultrasonic vibrator comprising:

a transducer having a braking capacity component constructed by connecting a plurality of vibrating elements for converting a driving current into vibrations;

a capacitive component portion connected in parallel with said transducer;

a plug detachably connected to an ultrasonic drive generating portion for generating said driving current; and an electric power supply cord for supplying said driving current from said plug to said transducer;

wherein a composite capacity value of said braking capacity component and a capacity component of said capacitive component portion is turned into a capacitive component value that offsets an inductive component disposed in said ultrasonic drive generating portion, and said capacitive component portion is disposed in an inside of said plug.

4. An ultrasonic vibrator comprising:

a transducer having a braking capacity component constructed by connecting a plurality of vibrating elements for converting a driving current into vibrations;

a capacitive component portion connected in parallel with said transducer;

a plug detachably connected to an ultrasonic drive generating portion for generating said driving current; and an electric power supply cord for supplying said driving current from said plug to said transducer;

wherein, a composite capacity value of said braking capacity component and a capacity component of said capacitive component portion is turned into a capacitive component value that offsets an inductive component disposed in said ultrasonic drive generating portion, and said capacitive component portion is disposed in apart of said electric power supply cord.

* * * * *